United States Patent [19]

Chen

[11] Patent Number: 5,097,255
[45] Date of Patent: Mar. 17, 1992

[54] CARRYING SECURITY DEVICE FOR MEDICAL DROPPER

[76] Inventor: I-Cheng Chen, 2 Fl., No. 6, Alley 8, Szewei Hsiang, Chungcheng Rd., Hsin Tien, Taipei, Taiwan

[21] Appl. No.: 617,697

[22] Filed: Nov. 26, 1990

[51] Int. Cl.$^5$ .............................................. G08B 21/00
[52] U.S. Cl. .................................. 340/603; 340/573; 340/539; 340/618; 128/DIG. 13
[58] Field of Search ............... 340/539, 573, 608, 603, 340/618; 128/DIG. 13; 73/290 R; 137/551, 558

[56] References Cited

U.S. PATENT DOCUMENTS

| | | | |
|---|---|---|---|
| 3,739,943 | 5/1973 | Wilhelmson et al. | 128/DIG. 13 X |
| 3,832,998 | 9/1974 | Gregg | 128/DIG. 13 X |
| 4,800,370 | 1/1989 | Vetechik | 340/573 |

Primary Examiner—Jin F. Ng
Assistant Examiner—Jeffery A. Hofsass
Attorney, Agent, or Firm—Asian Pacific International Patent and Trademark Office

[57] ABSTRACT

A carrying safety device for a medical dropper, having a housing, a lifting/lowering controller, a dropper bottle and an auto-controlling system, wherein the housing has several chambers and provided with two ring buckles, in connection with a carrying belt for placing on the patient's back; the lifting/lowering controller is located in the housing with an extending/retracting portion extending outside the housing; the dropper bottle is connected with and controlled by the extending/retracting portion to be raised above the patient's chest or lowered into the housing; the auto-controlling system is disposed with operating switches and an encoder on an operating panel mounted on the housing or on the carrying belt, and includes a lifting/lowering drive circuit, a signal transmitter and receiver; the signal transmitter has an encoder set-up with a transmitter code and a mercury balance switch whereby an emergency rescue signal may be transmitted; a manual switch is provided for the patient to activate the rescue signal, and a detecting circuit emitting a warning sound when the dropper injection is completed, the signal receiver being placed within an inspection range of a guard to receive the rescue signal and emit warning sounds to inform the guard. An LED display is being disposed to display the transmitter code.

11 Claims, 5 Drawing Sheets

CARRYING SECURITY DEVICE FOR MEDICAL DROPPER

BACKGROUND OF THE INVENTION

The present invention relates to a carrying security device for medical dropper and more particularly to a carrying security device for medical dropper, wherein in case of any accident, a nurse or a patient relative is informed to take care of the patient.

A great drawback exists in conventional medical dropper, i.e., the movement of the patient carrying the dropper is always greatly limited. Especially, when the patient goes to a toilet, great inconvenience takes place. On such occasion, it is quite troublesome that the dropper must be held by the patient himself/herself or by a nurse. Moreover, the dropper must be raised above the chest of the patient. Otherwise, danger might be caused. Suffering from such inconvenience for a long time, any patient will get a bad mood and consequently, the recovery of the patient will be inevitably affected. Furthermore, in case that an accident happens when the patient moves, the patient relatives or medical workers may be unaware of such conditions so that the patient may be threated with death. In conclusion, the conventional medical dropper is quite unsatisfactory.

SUMMARY OF THE INVENTION

It is an object of this invention to provide a medical dropper security device which permits the patient to safely walk or move with the dropper carried on his/her back and in case any unexpected situation happens, the guarder of the patient will be informed to immediately take care of the patient.

The present invention can be best understood through the following description and accompanying drawings wherein:

DETAILED DESCRIPTION OF THE PREFERRED EMBODIMENT

Figure 1:
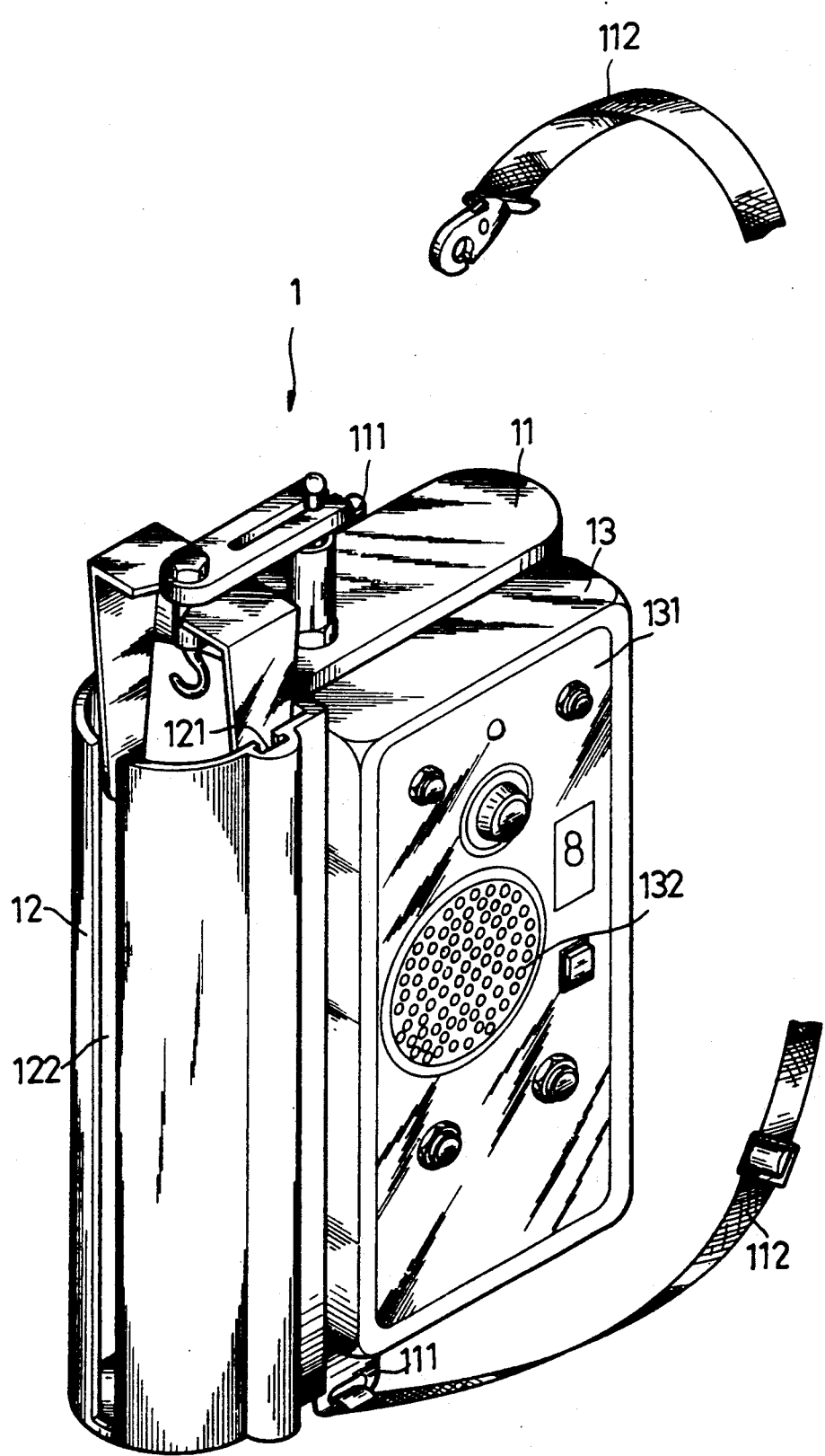
FIG. 1 is a perspective view of the medical dropper security device of this invention.

Please first refer to FIG. 1, wherein the present invention includes a housing 1 for a medical dropper, composed of a lifting/lowering controller chamber 11, a dropper chamber 12 and an auto-controlling system chamber 13. The controler chamber 11 is located on inner side of the housing 1 and at upper and lower ends of the chamber 11 are disposed two ring buckles 111 each of which connects with one end of a carrying belt 112 so that a patient can move, carrying the housing 1 on his/her back by means of the carrying belt 112. The dropper chamber 12 is located on left side of the housing 1. Inside the dropper chamberr 12, two grooved rails 121 are formed on the front and rear sides thereof, and a long slot 122 is formed on left side of the dropper chamber 12. The auto-controlling system chamber 13 is located on outer side of the housing 1 with an operation panel 131 and speaker opening 132 disposed thereon.

Figure 2:
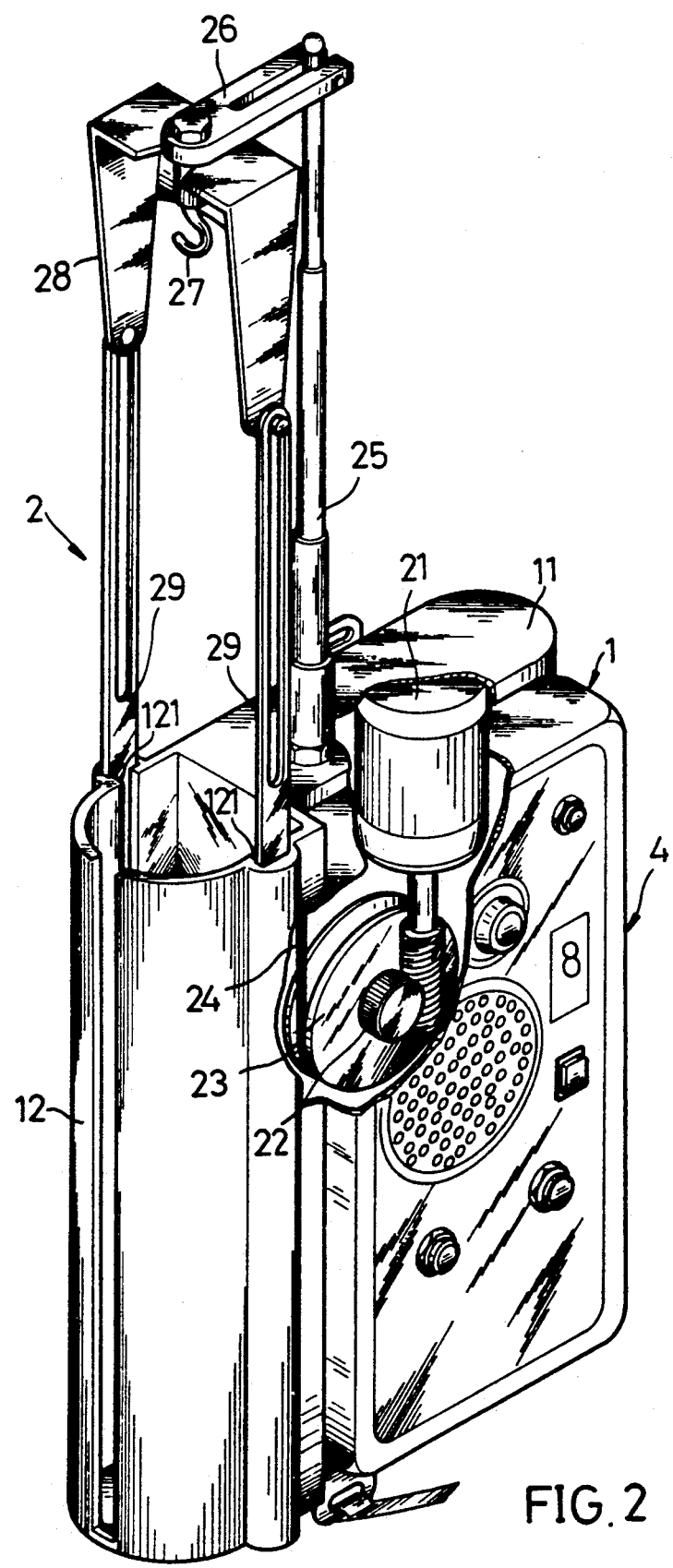
FIG. 2 is a view according to FIG. 1, showing the lifting/lowering controller of the security device of this invention.

Please refer to FIG. 2 now. The lifting/lowering controller 2 includes a drive motor 21, a reducing gear set 22, a take-up drum 23, a firm nylon cord 24, a telescopic antenna 25, a hanger beam 26, a hanger hook 27, a U-shaped member 28 and two long strips 29. The drive motor 21 cooperates with the reducing gear set 22 to drive the takeup drum 23 to take up the nylon cord 24 for extending/retracting the antenna 25. The hanger beam 26 is perpendicular to the antenna 25 and the hanger hook 27 connects with the hanger beam 26 and vertically faces downward. The U-shaped member 28 also connects with the hanger beam 26 at its upper central portion and vertically faces downward. The upper ends of the long strips 29 are connected with two leg portions of the U-shaped member 28 and can move within and along the groove rails 121 to extend outward and retract inward.

Figure 3:
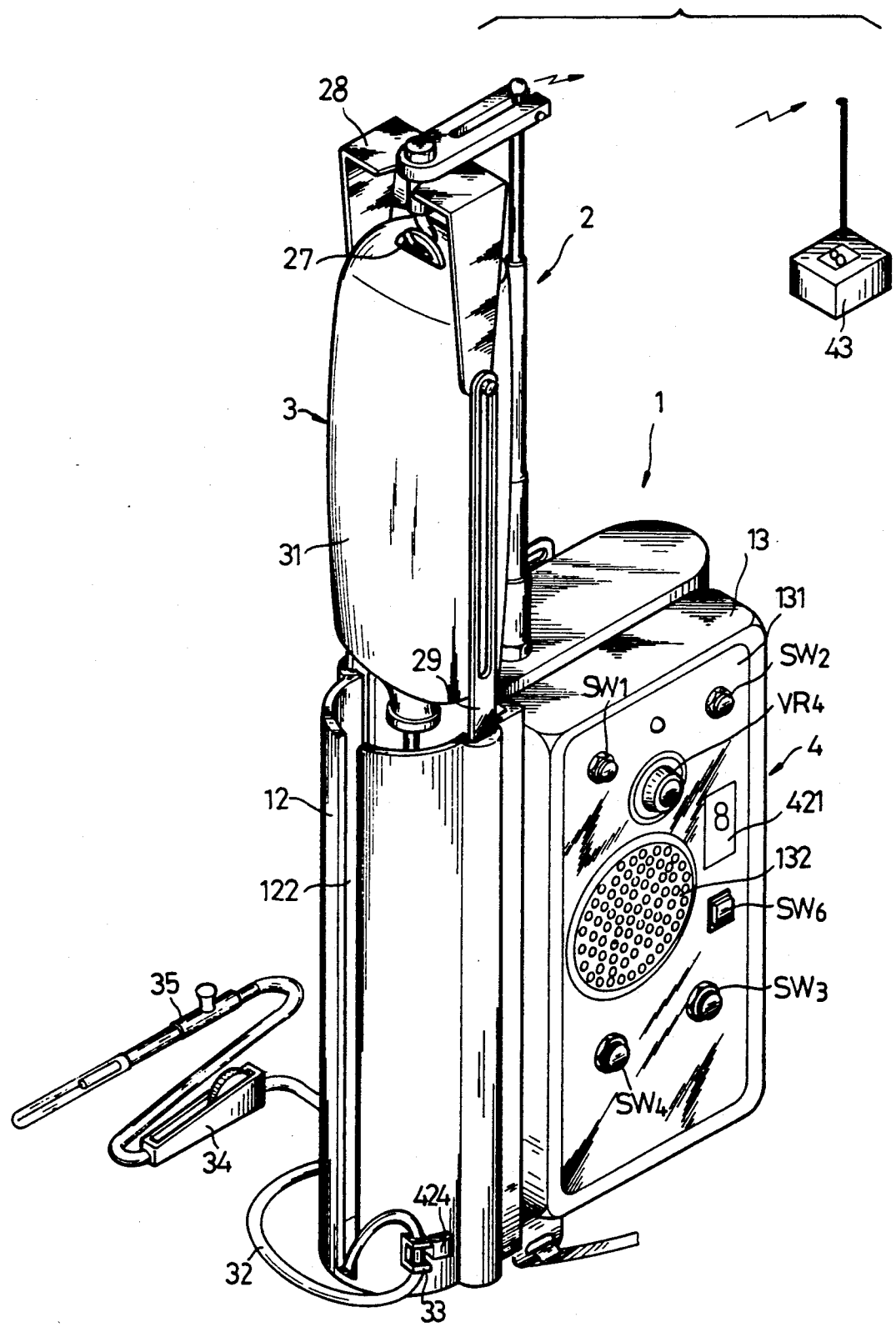
FIG. 3 i a view also according to FIG. 1, showing the arrangement of the security device of this invention.

Please now refer to FIG. 3, wherein a medical dropper 3 includes a dropper bottle 31, a dropper hose 32, a fixing clip 33, a flow controller 34 and a syringe 35. The dropper bottle 31 is placed in the dropper chamber 12 of the housing 1. The bottom of the dropper bottle 31 is hung on the hook 27 and protected by the U-shaped member 28 and long strips 29 to avoid swinging movement of the dropper bottle 31. The dropper hose 32 is placed within the slot 122 with one end connected with the dropper bottle 31 and middle portion clamped by the fixing clip 33 and fixed at outer lower portion of the chamber 12. The flow controller 34 is connected with the hose 32 near the other end of the hose 32. The syringe 35 is connected with the other end of the hose 32. The auto-controlling system 4 is composed of a power source 40, a lifting/-lowering drive circuit 41, a signal transmitter 42 and a signal receiver 43. The power source 40, lifting/lowering drive circuit 41 and transmitter 42 are disposed in the auto-controlling system chamber 13 with several operating switches SW1, SW2, SW3, SW4, SW6, VR4 and an encoder 421 disposed on the operation panel 131 or the carrying belt 112 or externally disposed (for wireless or wired control) for the convenience of operation under carrying condition. A speaker 420 is disposed in the speaker opening 132. The signal receiver 43 is located within an inspection range of a guarder so that in case of any accident, the guarder can immediately go and and take care of the patient.

Figure 4:
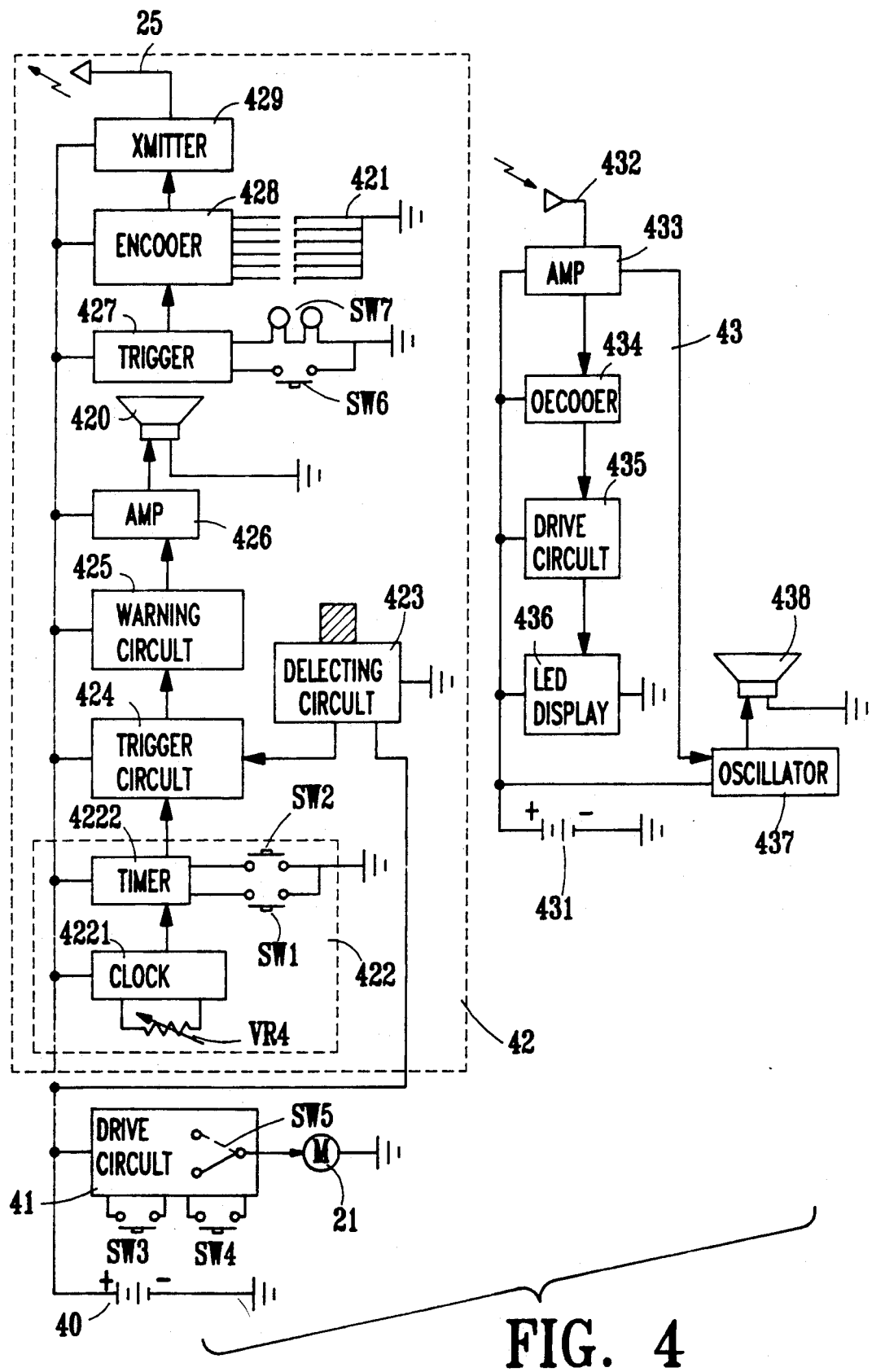
FIG. 4 is a block diagram of the auto-controlling system of the security device of this invention.

Please now refer to FIG. 4, wherein a block circuit diagram of the auto-controlling system 4 is shown. The power source 40 of the auto-controlling system 4 supplies power for the lifting/lowering drive circuit 41 and signal transmitter 42 to keep the circuit in a standby state during c normal time. The lifting/lowering drive circuit 41 is composed of continuous switches SW3, SW4 and sensitive switch SW5 which cooperate with the drive motor 21 or the lifting/lowering controller 2 for driving the dropper bottle 31 hanged on the hook 27 upward and lifting the same to a position over the chest of patient for facilitating the dropper injection. The dropper bottle 31 can also be lowered to be contained in the dropper chamber 12. The signal transmitter 42 is composed of a timing circuit 422, a trigger circuits 424, 427, a warning circuit 425, an amplifying circuit 426, the speaker 420, an encoder circuit 428 and a transmitter cirucit 429, wherein the timing circuit 422 is composed of a time base clock 4221, a timer 4222, a time adjusting switch VR4, the start switch SW1 and the reset switch SW2. The timing circuit 422 can be previously set up with a certain period of time. When the time is up, the timing circuit 422 outputs a signal through the trigger circuit 424, warning circuit 425 and amplifying circuit 426 to the speaker 420. The speaker 420 will accordingly emit warning sound to remind the patient to take care. The trigger circuit 424 can connect with a detecting circuit 423 for detecting the injection condition. Before the injection is completed, the detecting circuit will output a signal through the trigger circuit 424, warning circuit 425 and amplifying circuit 426 to the speaker 420 for emitting warning sound to remind the patient to take care. The trigger circuit 427 can connect with a mercury balance switch SW7 whereby in case the patient falls down, the balance switch SW7 will output a signal through the encoder circuit 428 to the transmitter circuit 428 and the antenna 25 will emit a rescue signal. The trigger circuit 427 can also be connected with the manual switch SW6 whereby in case of any accident, the patient only needs to activate the manual switch SW6 to send out a rescue signal. The encoder circut 428 can connect with an encoder 421 and a transmitter code can be preset whereby the rescue signal can go through the encoder circuit 428 and transmitter circuit 429 to be sent out by the telescopic antenna 25. The signal receiver 43 is composed of a power source 431, a receiving antenna 432, a receiving amplifying circuit 433, a decoder circuit 434, a drive circuit 435, an LED display 436, an oscillating cirucit 437 and a speaker 438, wherein the power source 431 supplies power for the circuit to keep the same in a standby state during a normal time, and the rescue signal sent by the transmitter 42 is received by the receiving antenna 432 and amplified by the receiving amplifying circut 433 and is decoded by the decoder circuit 434. After the transmitter code is decoded, the drive circuit 435 works and the LED display 436 displays the transmitter code and outputs a signal to activate the oscillating circuit 437 to produce oscillation for the speaker 438 to emit warning sound to inform the guarder of the situation for immediately taking care of the patient. By means of the transmitter code, the guarder can know which patient is situated at the accident.

Figure 5:
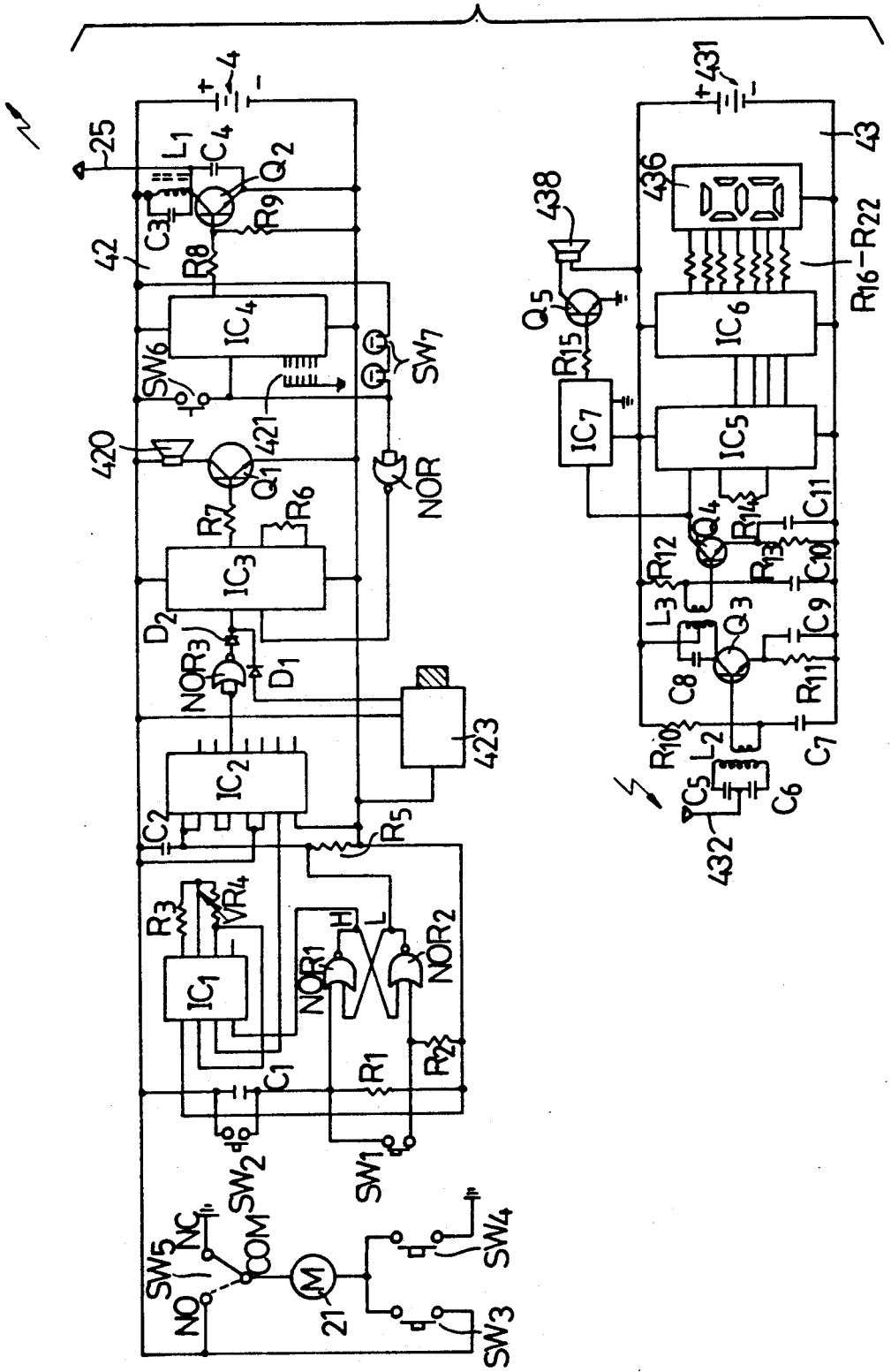
FIG. 5 is a circuit diagram of the auto-controlling system thereof.

Please now refer to FIG. 5 which shows the circuit diagram of the auto-controlling system, wherein the power source 40 supplies power for the circuit to keep the same in a standby state during a normal time. When pressing down the continuous switch SW3, the positive electrode is grounded through the drive motor 21 and COM and NC terminals of the sensitive switch SW5, producing a circuitry to make the drive motor 21 reversely rotate so as to downward drive the lifting/lowering controller 2 to a fixed position, and a leaf spring of the sensitive switch SW5 jumps away, restoring to its home position so as to disconnect the COM and NO terminals and stop the driving. The COM and NC terminals are connected to wait or next activation. When start switch SW1 is pressed, nor gates NOR1, NOR2 will output positive signal to integrated circuit IC1. The circuit IC1 and nor gates NOR1, NOR2 form a multivibrator circuit to produce time base pulse and is set up with required time by means of the time adjusting switch VR4. (The time constant is determined by switch VR4.) Each oscillating signal is input into an integrated circuit IC2 which serves as a counter and outputs a signal through a reverser NOR3 to the integrated circuit IC3 when the preset time is up. Integrated circuit IC3 is formed by an LSI sound IC and a trigger circuit, capable of outputting warning signal through resistor R7 to be amplified by transistor Q1 for driving the speaker 420 to emit warning sound for reminding the patient to attend to that the time is up. When it is desired to stop the warning sound or reset the time, one only needs to press the reset switch SW2 to stop the warning sound or reset the time. When the detecting circuit 423 detects that the dropper injection is about completed, a signal is output to acctivate IC3 to emit warning sound to remind the patient to attend to that the dropper injection is about completed. The diode Q1 is for preventing the signal output from NOR3 from being input to the detecting circuit 423, an diode Q2 is for preventing the signal output from the detecting circuit 423 from being input to NOR3. In case that the patient loses his/her balance due to falling down, the mercury balance switch SW7 will become short and positive power is input to integrated circuit IC4 through the mercury balance switch SW7. IC4 is a trigger and encoding type of IC and is connected with an encoder 421. A transmitter code can be previously set. When IC4 is activated, a rescue signal and a preset transmitter code signal are output through resistor R8 and a high frequency transmitting circuit formed by transistor Q2, oscillating coil L1, capacitors C3, C4 to the telescopic antenna 25. The antenna 25 then transmits out the signal. The mercury balance switch SW7 also outputs a signal through reverser NOR4 to IC3 for emitting warning sound. In case of any unexpected situation, the manual switch SW6 can be activated and the positive power is input to IC4 through SW6 for sending out rescue signal. At this time, the IC3 is also activated to emit warning sound. When the receiving antenna 432 receives the rescue signal, the parallel capacitors C5, C6 and oscillating coil L2 will produce local oscillation and remove carrier. The signal is then sent to transistor Q3 for amplification and is further amplified by serially connected capacitor C8, oscillating coil L3 and transistor Q4 to activate integrated circuit IC7. IC7 is a sound IC oscillating circuit which can output warning signal through resistor R15 to be amplified by transistor Q5 to drive speaker 438 for emitting warning sound. The rescue signal is also input to integrated circuit IC5 which is a decoder circuit, capable of decoding the transmitter code set in the signal transmitter. The decoded signal is driven by the integrated circuit IC6 and a voltage drop occurs through R16 to R22 and LED display 436 works to show the code of the transmitter, making the guarder realize which patient is in danger. The power source 431 supplies power for the circuit and keeps the circuit in standby state so as to readily receive rescue signal in any time.

While a preferred embodiment has been shown and described, it will be understood that there is no intent to limit the invention by such disclosure, but rather it is intended to cover all modifications and alternate constructions falling within the spirit and the scope of the invention as defined in the appended claims.

What is claimed is:

1. A carrying security device for a medical dropper comprising:
   a housing including a lifting/lowering controller chamber disposed on the inner side of said housing, a dropper chamber disposed on the left side of said housing, and an auto-controlling system chamber disposed on the front side of said housing, inside said dropper chamber, on the front and rear sides thereof are formed two grooved rails and on the left side of said dropper chamber is formed a slot on the surface of said auto-controlling system being disposed an operating panel and a speaker opening;

a lifting/lowering controller including a drive motor, a reducing gear set, a take-up drum, a firm nylon cord, a telescopic antenna, a hanger beam, a hanger hook, a U-shaped protecting member and two long protecting strips, wherein said drive motor cooperating with said reducing gear is set for driving said take-up drum to take up said nylon cord so as to extend/retract said telescopic antenna, said antenna being disposed in said controller chamber with its extensible portion extending outside said controller chamber when extended, said hanger beam being perpendicularly associated with the head of said telescopic antenna, said hanger hook being connected with said hanger beam and extending vertically downward, said U-shaped protecting member being connected with said hanger beam at upper central portion and extending vertically downward, said protecting strips being connected respectively with two legs of said U-shaped member, said protecting strips being movable within said grooved rails of said dropper chamber and capable of extending outward/retracting inward along said grooved rail;

an injection dropper including a dropper bottle, a hose, a fixing clip, a flow controller and a syringe, wherein said dropper bottle is disposed in said dropper chamber with its bottom hung on said hanger hook of said lifting/lowering controller, said hose being disposed within said slot of said dropper chamber with its one end connected with said dropper bottle and its middle portion clamped by said clip at outer lower portion of said dropper chamber and its other end connected with said syringe, said flow controller being connected near the other end of said hose; and an auto-controlling system including a lifting/lowering drive circuit, a signal transmitter, and a signal receiver, wherein said drive circuit cooperates with said lifting/lowering controller or lifting said dropper bottle hung on said hook to position over the chest of a patient to facilitate and injection, and for lowering said dropper bottle into said dropper chamber, said signal transmitter being in a standby state at a normal time and producing a rescue signal in an accident state, said rescue signal being transmitted by said telescopic antenna of said lifting/lowering controller, several operating switches and an encoder being disposed on said operating panel, a speaker being disposed in said speaker opening, said signal receiver being in a standby state at a normal time when receiving said rescue signal sent from said signal transmitter, said signal receiver processing the rescue signal and emittig warning sound to inform a guard and an LED display displaying a transmitter code so that the guard can realize which patient is in an accident condition, said signal receiver being placed within an inspection rage of the guard.

2. A carrying security device as claimed in claim 1, wherein at upper and lower ends of said housing are respectively disposed two ring buckles and a carrying belt is connected with said ring buckles for a user to carry said security device on his/her back.

3. A carrying security device as claimed in claim 1, wherein the bottom of said housing is plane and suitable to be placed on any plane article.

4. A carrying security device as claimed in claim 1, wherein an encoder is disposed with said signal transmitter and a transmitter code can be set in said encoder and transmitted therefrom and received by said signal receiver and displayed by said LED display.

5. A carrying security device as claimed in claim 1, wherein a mercury balance switch is disposed with said signal transmitter whereby in case the patient loses his/her balance and falls down, a rescue signal is tranmitted out.

6. A carrying security device as claimed in claim 1, wherein a manual switch is disposed with said signal transmitter whereby in case of any accident, the patient can activate said manual switch to transmit a rescue signal.

7. A carrying security device as claimed in claim 1, wherein a timing circuit is disposed with said signal transmitter whereby a period of time can be preset and when the time is up, a warning sound is emitted to remind the patient.

8. A carrying security device as claimed in claim 1, wherein a detecting circuit is connected with said signal transmitter and fixed on outer lower portion of said dropper chamber of said housing for monitoring said dropper hose whereby when the dropper injection is about completed, a signal is output to said signal tranmitter for emitting as a reminder warning sound to the patient.

9. A carrying security device as claimed in claim 1, wherein said operating switches are disposed on a carrying belt for the convenience of operation in the state of carrying the device on one's back.

10. A carrying security device as claimed in claim 1, wherein said operating switches are disposed externally.

11. A carrying security device as claimed in claim 1, wherein one guard can at a time take care of several such security devices.

* * * * *